(12) United States Patent
Bentley et al.

(10) Patent No.: US 6,288,011 B1
(45) Date of Patent: Sep. 11, 2001

(54) 1,4-DIARYL-2,3-DIFLUORO-2-BUTENE INSECTICIDAL AND ACARICIDAL AGENTS

(75) Inventors: Terence James Bentley, East Windsor, NJ (US); Keith Douglas Barnes, Newtown, PA (US)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/189,545

(22) Filed: Nov. 11, 1998

Related U.S. Application Data

(60) Provisional application No. 60/065,127, filed on Nov. 12, 1997.

(51) Int. Cl.[7] .......................... A01N 31/00; A01N 31/14; C07C 41/00; C07C 19/08
(52) U.S. Cl. .......................... 504/352; 568/639; 568/635; 568/637; 568/638; 504/351; 570/128; 514/717; 514/718; 514/720; 514/721
(58) Field of Search .................. 568/639, 635, 568/637, 638; 504/351, 352; 514/717, 718, 720, 721; 570/128

(56) References Cited

U.S. PATENT DOCUMENTS 5,248,834    9/1993    Elliott et al. .................. 528/638

FOREIGN PATENT DOCUMENTS

| 2228803-A | 11/1995 | (GB) | ............ C07C/43/225 |
|---|---|---|---|
| 0 811 593 A1 | 12/1997 | (GB) | ............ C07C/25/24 |
| WO 94/06741 | 3/1994 | (WO) | ............ C07C/43/29 |
| WO 97/16067 | 5/1997 | (WO) | ............ A01N/31/14 |

OTHER PUBLICATIONS

D.J. Burton, et al., Journal of the American Chemical Society 102:11 (May 1980).

*Primary Examiner*—Sreeni Padmanabhan
*Assistant Examiner*—J. Parsa
(74) *Attorney, Agent, or Firm*—Joseph M. Mazzarese; Barbara V. Maurer

(57) ABSTRACT

Pesticidal 1,4-diaryl-2,3-difluoro-2-butene compounds having the structural formula I

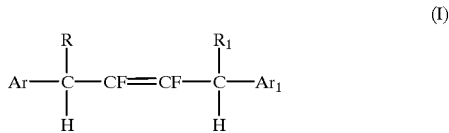

and compositions and methods comprising those compounds for the control of insect and acarid pests.

26 Claims, No Drawings

1,4-DIARYL-2,3-DIFLUORO-2-BUTENE INSECTICIDAL AND ACARICIDAL AGENTS

This application claims the benefit of the Nov. 12, 1997 filing date of Provisional Application Ser. No. 60/065,127 under 35 U.S.C 119(e).

BACKGROUND OF THE INVENTION

Insect and acarid pests destroy growing and harvested crops. In the United States, agronomic crops must compete with thousands of those pests. In particular tobacco budworms, southern armyworms and corn rootworms are especially devastating to crops. In spite of the commercial insecticides and acaricides available today, damage to crops, both growing and harvested, caused by insect and acarid pests still occurs. Accordingly, there is ongoing research to create new and more effective insecticidal and acaricidal agents.

Certain fluoroolefin compounds are known to possess insecticidal and acaricidal activity (see, e.g., U.S. Pat. No. 5,248,834; GB 2,288,803-A; WO 94/06741; WO 97/16067 and co-pending U.S. patent application Ser. No. 08/865,244 filed on May 29, 1997. However, the fluoroolefin compounds disclosed in those patents and patent applications are outside the scope of the present invention. U.S. Pat. No. 5,248,834 generically discloses certain 1-aryl-1-(3-aryl-1,2-difluoroprop-1-enyl)cyclopropane compounds. However, that patent does not provide a method to prepare those compounds. In fact, U.S. Pat. No. 5,248,834 does not provide a method to prepare any fluoroolefin compounds.

It is, therefore, an object of the present invention to provide compounds which are highly effective for the control of insect and acarid pests.

It is also an object of the present invention to provide a method for the control of insect and acarid pests.

It is a further object of this invention to provide a method for the protection of growing and harvested crops from damage caused by insect and acarid attack and infestation.

Those and other objects of the present invention will become more apparent from the detailed description thereof set forth below.

SUMMARY OF THE INVENTION

The present invention comprises 1,4-diaryl-2,3-difluoro-2-butene compounds which are useful as insecticidal and acaricidal agents. Those compounds are also useful for protecting plants from damage caused by insect and acarid attack and infestation.

The 1,4-diaryl-2,3-difluoro-2-butene compounds of the present invention have the structural formula I

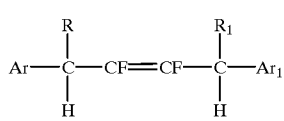

(I)

wherein
Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups,
   1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
   a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is hydrogen, $C_1$–$C_4$alkyl, $C_1$–$C_4$haloalkyl, $C_3$–$C_6$cycloalkyl or $C_3$–$C_6$halocycloalkyl;
$R_1$ is hydrogen, F, Cl, Br, cyano or $OR_2$;
$R_2$ is hydrogen or $C_1$–$C_4$alkyl; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
   phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
   biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
   phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
   benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
   benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
   benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
   1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
   a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and
the optical isomers thereof, and
the (E)- and (Z)-isomers thereof.

This invention also comprises compositions containing those compounds and methods for using those compounds and compositions. Advantageously, it has been found that the 1,4-diaryl-2,3-difluoro-2-butene compounds of the present invention, and compositions containing them, are useful for the control of insect and acarid pests. The compounds of this invention are also useful for the protection of plants from damage caused by insect and acarid attack and infestation.

DETAILED DESCRIPTION OF THE INVENTION

The present invention provides a method for the control of insect or acarid pests which comprises contacting said pests or their food supply, habitat or breeding grounds with a pesticidally effective amount of a 1,4-diaryl-2,3-difluoro-2-butene compound of formula I.

The present invention also provides a method for the protection of growing plants from attack or infestation by insect or acarid pests which comprises applying to the foliage of the plants, or to the soil or water in which they are growing, a pesticidally effective amount of a 1,4-diaryl-2,3-difluoro-2-butene compound of formula I.

The 1,4-diaryl-2,3-difluoro-2-butene compounds of the present invention have the structural formula I

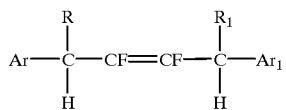

(I)

wherein Ar, $Ar_1$, R and $R_1$ are as described hereinabove for formula I.

In formula I above, 5- and 6-membered heteroaromatic rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted as described in formula I above.

Exemplary of halogen hereinabove are fluorine, chlorine, bromine and iodine. The terms "$C_1$–$C_4$haloalkyl", "$C_3$–$C_6$halocycloalkyl" and "$C_1$–$C_4$haloalkoxy" are defined as a $C_1$–$C_4$alkyl group, a $C_3$–$C_6$cycloalkyl group and a $C_1$–$C_4$alkoxy group substituted with one or more halogen atoms, respectively.

Preferred formula I pesticidal agents of this invention are those wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is $C_1$–$C_4$alkyl, $C_1$–$C_4$haloalkyl, $C_3$–$C_6$cycloalkyl or $C_3$–$C_6$halocycloalkyl;

$R_1$ is hydrogen, F, Cl, Br, cyano or $OR_2$;

$R_2$ is hydrogen or $C_1$–$C_4$alkyl; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

More preferred 1,4-diaryl-2,3-difluoro-2-butene compounds of this invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl, trifluoromethyl or cyclopropyl;

$R_1$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Most preferred insecticidal and acaricidal agents of the present invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl;

$R_1$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Formula I compounds of this invention which are particularly effective insecticidal agents include 4-(p-chlorophenyl)-2,3-difluoro-5-methyl-1-(m-phenoxyphenyl)-2-hexene, (E)-;

4-(p-chlorophenyl)-2,3-difluoro-1-(4-fluoro-3-phenoxyphenyl)-5-methyl-2-hexene, (E)-;

2,3-difluoro-5-methyl-1-(m-phenoxyphenyl)-4-[p-(trifluoromethoxy)phenyl]-2-hexene, (E)-;

4-(p-ethoxyphenyl)-2,3-difluoro-1-(m-phenoxyphenyl)-5-methyl-2-hexene, (E)-;

4-(p-ethoxyphenyl)-2,3-difluoro-1-(4-fluoro-3-phenoxyphenyl)-5-methyl-2-hexene, (E)-;

2,3-difluoro-1-(4-fluoro-3-phenoxyphenyl)-5-methyl-4-[p-(trifluoromethoxy)phenyl]-2-hexene, (E)-;

2,3-difluoro-4-(p-fluorophenyl)-5-methyl-1-(m-phenoxyphenyl)-2-hexene, (E)-; and 2,3-difluoro-1-(4-fluoro-3-phenoxyphenyl)-4-(p-fluorophenyl)-5-methyl-2-hexene, (E)-, among others.

The 1,4-diaryl-2,3-difluoro-2-butene compounds of this invention are especially useful for the control of tobacco budworms, southern armyworms and corn rootworms.

In a preferred embodiment of the present invention, the fluorine atoms attached to the carbon atoms of the double bond in the formula I compounds are in the (E)-configuration with respect to each other.

Formula I compounds wherein $R_1$ is hydrogen may be prepared, as illustrated in Flow Diagram I, by reacting a 3-aryl-1,1,2-trifluoro-1-propene compound of formula II with sodium bis(2-methoxyethoxy)aluminum hydride and a mineral acid such as hydrochloric acid to form a 3-aryl-1,2-difluoro-1-propene compound of formula III, and sequentially reacting the formula III compound with an alkyllithium such as n-butyllithium, zinc chloride, tetrakis(triphenylphosphine)palladium(0) and a substituted methyl halide of formula IV.

FLOW DIAGRAM I

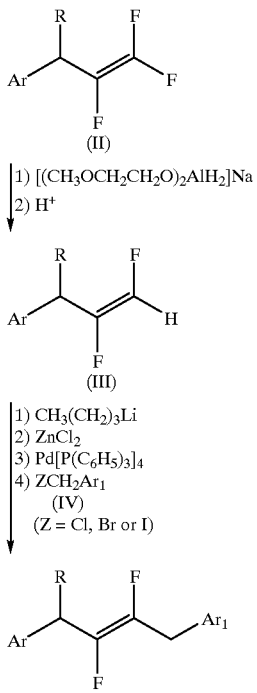

Formula I compounds wherein $R_1$ is hydroxy may be prepared, as shown in Flow Diagram II, by reacting a 3-aryl-1,2-difluoro-1-propene compound of formula III with an alkyllithium such as n-butyllithium and an aldehyde of formula V.

FLOW DIAGRAM II

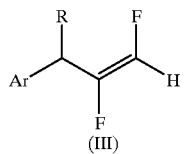
(III)

1) CH$_3$(CH$_2$)$_3$Li
2) Ar$_1$CHO
(V)

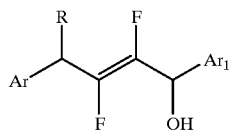

Formula I compounds wherein the fluorine atoms about the double bond are in the (Z)-configuration may be prepared by isomerizing the formula III compounds described hereinabove which are predominately in the (E)-configuration using conventional procedures such as exposure to light.

Compounds of formula I wherein R$_1$ is F, Cl or Br may be prepared by reacting a formula I compound wherein R$_1$ is hydroxy with thionyl chloride, thionyl bromide or diethylaminosulfur trifluoride. The reaction scheme is shown below in Flow Diagram III.

FLOW DIAGRAM III

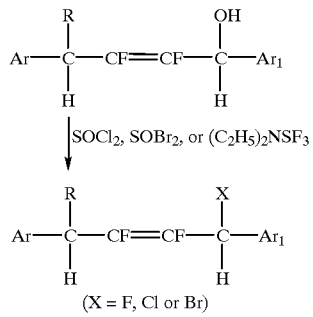
(X = F, Cl or Br)

Alternatively, formula I compounds wherein R$_1$ is Cl or Br may be prepared by halogenating a formula I compound wherein R$_1$ is hydrogen with a chlorinating agent such as N-chlorosuccinimide or a brominating agent such as N-bromosuccinimide. The reaction scheme is shown below in Flow Diagram IV.

FLOW DIAGRAM IV

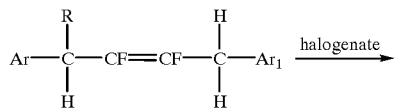

-continued

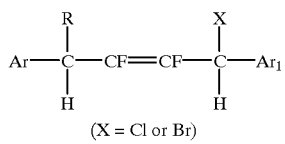
(X = Cl or Br)

Formula I compounds wherein R$_1$ is cyano may be prepared by reacting a formula I compound wherein R$_1$ is F, Cl or Br with sodium cyanide. The reaction scheme is shown in Flow Diagram V.

FLOW DIAGRAM V

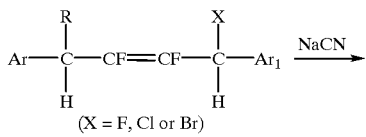
(X = F, Cl or Br)

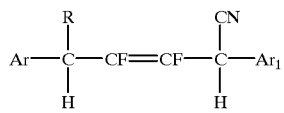

Alternatively, formula I compounds wherein R$_1$ is cyano may be prepared, as illustrated in Flow Diagram VI, by reacting a formula I compound wherein R$_1$ is hydroxy with methanesulfonyl chloride (mesyl chloride) or p-toluenesulfonyl chloride (tosyl chloride) in the presence of a base to form an intermediate compound of formula VI, and reacting the intermediate compound with sodium cyanide.

FLOW DIAGRAM VI

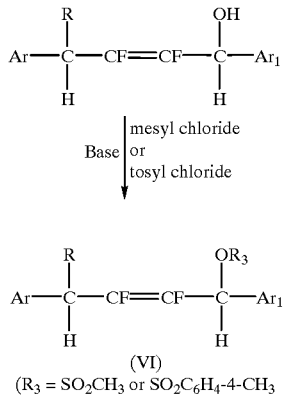

Base | mesyl chloride or tosyl chloride

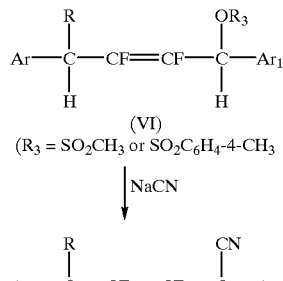
(VI)
(R$_3$ = SO$_2$CH$_3$ or SO$_2$C$_6$H$_4$-4-CH$_3$)

NaCN

Formula I compounds wherein R$_1$ is OR$_2$ may be prepared as shown below in Flow Diagram VII.

FLOW DIAGRAM VII

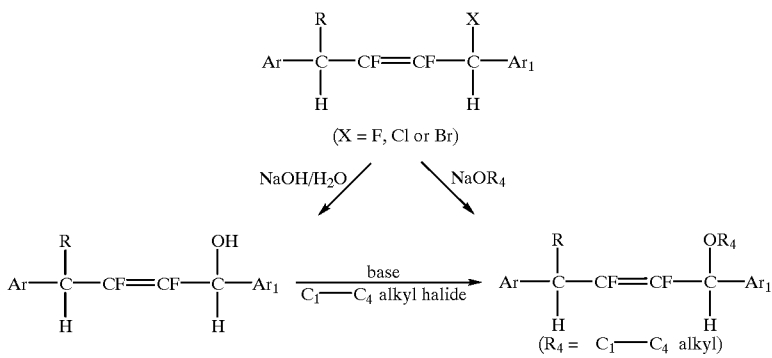

(X = F, Cl or Br)

Starting formula II compounds may be prepared, as shown in Flow Diagram VIII, by sequentially reacting bromotrifluoroethylene with zinc, copper(I) bromide and a substituted methyl bromide of formula VII or a trifluoroacetate of formula VIII.

FLOW DIAGRAM VIII

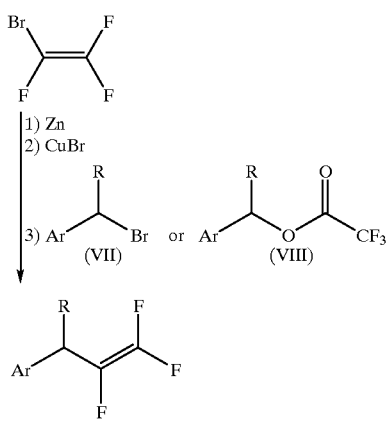

Intermediate compounds of formula VII may be prepared, as illustrated in Flow Diagram IX, by reacting an arylmagnesium bromide compound of formula IX with an aldehyde of formula X and a mineral acid to form an alcohol of formula XI, and reacting the formula XI alcohol with hydrobromic acid.

FLOW DIAGRAM IX

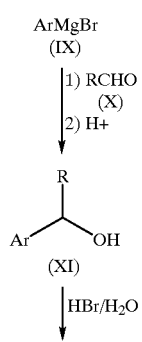

-continued

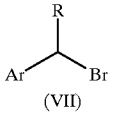
(VII)

Compounds of formula VIII may be prepared by reacting a formula XI alcohol with trifluoroacetic anhydride. The reaction scheme is shown in Flow Diagram X.

FLOW DIAGRAM X

Intermediate alcohols of formula XI may also be prepared, as shown in Flow Diagram XI, by reacting an aryl bromide of formula XII with an alkyllithium such as n-butyllithium and an aldehyde of formula X.

FLOW DIAGRAM XI

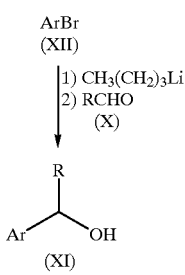

Other methods for the preparation of formula I compounds will become apparent from the examples set forth below.

The present invention also relates to intermediate compounds having the structural formula XIII

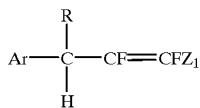
(XIII)

wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is hydrogen, $C_1$–$C_4$alkyl, $C_1$–$C_4$haloalkyl, $C_3$–$C_6$cycloalkyl or $C_3$–$C_6$halocycloalkyl; and
$Z_1$ is hydrogen or F, and
the optical isomers thereof, and
the (E)- and (Z)-isomers thereof.

Preferred intermediate compounds of formula XIII are those wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is $C_1$–$C_4$alkyl, $C_1$–$C_4$haloalkyl, $C_3$–$C_6$cycloalkyl or $C_3$–$C_6$halocycloalkyl; and
$Z_1$ is hydrogen or F.

More preferred formula XIII compounds are those wherein
Ar is phenyl optionally substituted with any combination of from one to three halogen, $C_1$-$C_4$alkyl, $C_1$–$C_4$haloalkyl, $C_1$–$C_4$alkoxy or $C_1$–$C_4$haloalkoxy groups;
R is isopropyl; and
$Z_1$ is hydrogen or F.

The 1,4-diaryl-2,3-difluoro-2-butene compounds of the present invention are effective for controlling insect and acarid pests. Those compounds are also effective for protecting growing or harvested crops from damage caused by insect and acarid attack and infestation.

Insects controlled by the 1,4-diaryl-2,3-difluoro-2-butene compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms, western corn rootworms and mustard beetles; and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites.

In practice generally about 10 ppm to about 10,000 ppm and preferably about 100 ppm to about 5,000 ppm of a formula I compound, dispersed in water or another liquid carrier, is effective when applied to plants or the soil in which the plants are growing to protect the plants from insect and acarid attack and infestation.

The 1,4-diaryl-2,3-difluoro-2-butene compounds of this invention are also effective for controlling insect and acarid pests when applied to the foliage of plants and/or to the soil or water in which said plants are growing in sufficient amount to provide a rate of about 0.1 kg/ha to 4.0 kg/ha of active ingredient.

While the compounds of this invention are effective for controlling insect and acarid pests when employed alone, they may also be used in combination with other biological chemicals, including other insecticides and acaricides. For example, the formula I compounds of this invention may be used effectively in conjunction or combination with pyrethroids, phosphates, carbamates, cyclodienes, endotoxin of Bacillus thuringiensis (Bt), formamidines, phenol tin compounds, chlorinated hydrocarbons, benzoylphenyl ureas, pyrroles and the like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a compound of the invention (or combinations thereof) admixed with one or more agronomically acceptable inert, solid or liquid carriers. Those compositions contain a pesticidally effective amount of said compound or compounds, which amount may vary depending upon the particular compound, target pest, and method of use. Those skilled in the art can readily determine what is a pesticidally effective amount without undue experimentation.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of p-Chloro-α-isopropylbenzyl alcohol

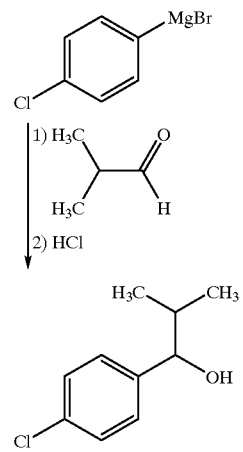

A 1 M solution of p-chlorophenylmagnesium bromide in diethyl ether (100 mL) is added to a solution of isobutyraldehyde (9.08 mL, 0.1 mol) in diethyl ether at −5 ° C. After the addition is complete, the reaction mixture is stirred overnight at room temperature, diluted with an ice-water mixture, and acidified with 10% hydrochloric acid. The phases are separated and the aqueous phase is extracted with diethyl ether. The organic phase and extracts are combined, washed sequentially with saturated sodium hydrogen carbonate solution, water and brine, dried over anhydrous sodium sulfate, and concentrated in vacuo to obtain an oil. Column chromatography of the oil using silica gel and a 33% methylene chloride in hexanes solution gives the title product as a colorless oil (14 g) which is identified by NMR spectral analyses.

Using essentially the same procedure, the following compounds are obtained:

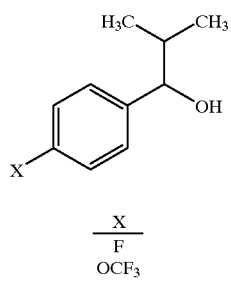

| X |
|---|
| F |
| OCF₃ |

EXAMPLE 2

Preparation of 1-(1-Bromo-2-methylpropyl)-4-chloro-benzyne

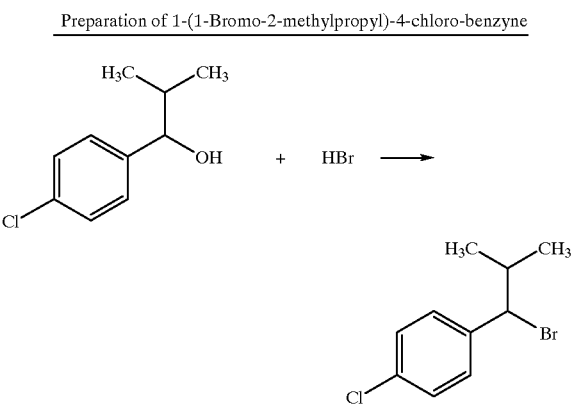

A mixture of p-chloro-α-isopropylbenzyl alcohol (33.08 g) in 48% hydrobromic acid (330 mL) is stirred at room temperature for 1 hour and extracted with hexanes. The combined organic extracts are washed sequentially with water, saturated sodium hydrogen carbonate solution and water, dried over anhydrous sodium sulfate, and concentrated in vacuo to give the title product as a yellow oil (42.98 g) which is identified by NMR spectral analysis.

Using essentially the same procedure, the following compounds are obtained:

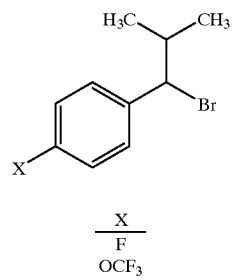

| X |
|---|
| F |
| OCF₃ |

EXAMPLE 3

Preparation of 3-(p-Chlorophenyl)-1,1,2-trifluoro-4-methyl-1-pentene

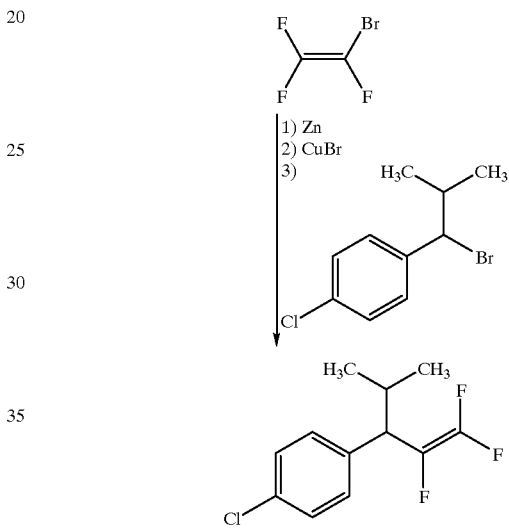

A mixture of zinc dust (15.72 g) and bromotrifluoroethylene (48.34 g, 0.30 mol) in N,N-dimethylformamide is heated to 38° C.. After stirring at 38° C. for several minutes, the reaction mixture temperature rises to 65° C. over 30 minutes. The reaction mixture is then stirred for 90 minutes and cooled to –5° C.. Copper(I) bromide (34.5 g, 0.24 mol) is then added to the cooled mixture. The reaction mixture is stirred at room temperature for 1 hour, treated sequentially with 1-(1-bromo-2-methylpropyl)-4-chlorobenzene (18.56 g, 0.075 mol) and limonene (5 drops), stirred at 49° C. overnight, cooled, and diluted with saturated ammonium chloride solution (400 mL) and concentrated ammonia solution (100 mL). The resultant aqueous mixture is extracted with hexanes. The combined organic extracts are washed sequentially with water, 10% hydrochloric acid, water, saturated sodium hydrogen carbonate solution and water, dried over anhydrous sodium sulfate, and concentrated in vacuo to obtain an oil. Column chromatography of the oil using silica gel and hexanes gives the title product as an oil (5.54 g) which is identified by NMR spectral analyses.

Using essentially the same procedure, the following compounds are obtained:

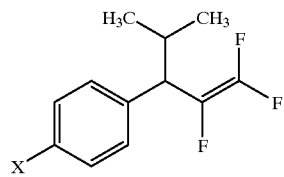

| X |
|---|
| F |
| OCF₃ |

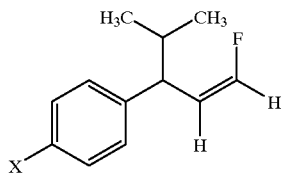

| X |
|---|
| F |
| OCF₃ |
| OC₂H₅ |
| OCH₃ |

In addition, when 1-(p-ethoxyphenyl)-2-methylpropyl trifluoroacetate and 1-(p-methoxyphenyl)-2-methylpropyl trifluoroacetate are substituted for 1-(1-bromo-2-methylpropyl)-4-chlorobenzene, 3-(p-ethoxyphenyl)-1,1,2-trifluoro-4-methyl-1-pentene and 3-(p-methoxyphenyl)-1,1,2-trifluoro-4-methyl-1-pentene are obtained, respectively.

EXAMPLE 4

Preparation of 3-(p-Chlorophenyl)-1,2-difluoro-4-methyl-1-pentene

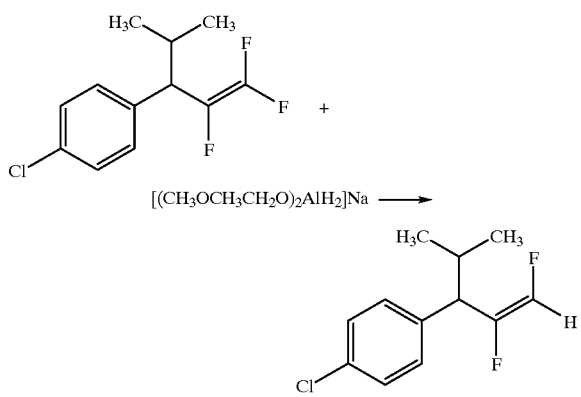

A solution of 3-(p-chlorophenyl)-1,1,2-trifluoro-4-methyl-1-pentene (2.48 g, 0.01 mol) in tetrahydrofuran is cooled to −8° C., treated dropwise with a 3.4 M solution of sodium bis(2-methoxyethoxy)aluminum hydride in toluene (3.1 mL), stirred overnight at room temperature, diluted with water, acidified with 10% hydrochloric acid, and extracted with methylene chloride. The combined organic extracts are washed sequentially with water, saturated sodium hydrogen carbonate solution and water, dried over anhydrous sodium sulfate, and concentrated in vacuo to obtain the title product as a yellow oil (2.10 g) which is identified by NMR spectral analyses.

Using essentially the same procedure, the following compounds are obtained:

EXAMPLE 5

Preparation of 4-(p-Chlorophenyl)-2,3-difluoro-5-methyl-1-(m-pehnoxyphenyl)-2-hexene, (E)-

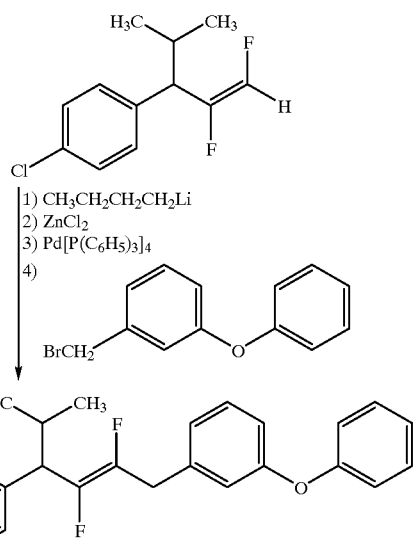

A solution of 3-(p-chlorophenyl)-1,2-difluoro-4-methyl-1-pentene (0.69 g, 0.003 mol) in tetrahydrofuran is cooled to −70° C., treated with a 2.5 M solution of n-butyllithium in hexane (1.2 mL), stirred at −60° C. for 1 hour, treated with a 0.5 M solution of zinc chloride in tetrahydrofuran (6 mL), stirred at −60° C. for 1 hour, treated sequentially with a solution of tetrakis(triphenylphosphine)palladium(0) (0.081 g) in tetrahydrofuran and a solution of α-bromo-m-tolyl phenyl ether (0.789 g, 0.003 mol) in tetrahydrofuran, stirred at room temperature overnight, diluted with water, acidified with 10% hydrochloric acid, and extracted with methylene chloride. The combined organic extracts are washed with water, dried over anhydrous sodium sulfate, and concentrated in vacuo to obtain an oil. Column chromatography of the oil using silica gel and pentane affords an oil which is purified by Kugelrohr distillation to give the title product as a pale, yellow oil (0.46 g) which is identified by NMR spectral analyses.

Using essentially the same procedure, the following compounds are obtained:

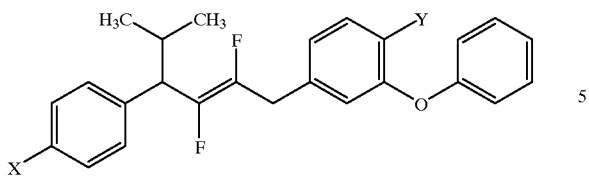

| X | Y | stats |
|---|---|---|
| Cl | F | colorless oil |
| OCF$_3$ | H | pale, yellow oil |
| OCF$_3$ | F | yellow oil |
| F | H | yellow oil |
| F | F | yellow oil |
| OC$_2$H$_5$ | H | colorless oil |
| OC$_2$H$_5$ | F | pale, yellow oil |
| OCH$_3$ | H | brown oil |

EXAMPLE 6

Preparation of p-Ethoxy-α-isopropylbenzyl alcohol

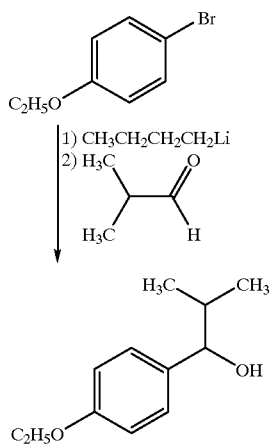

A solution of p-bromophenetole (2.01 g, 0.01 mol) in tetrahydrofuran is cooled to −65° C., treated dropwise with a 2.5 M solution of n-butyllithium in hexane (4 mL), stirred for 20 minutes at −55 to −65° C., treated dropwise with a solution of isobutyraldehyde (0.91 mL, 0.01 mol) in tetrahydrofuran, stirred overnight at room temperature, diluted with an ice-water mixture, acidified with 10% hydrochloric acid, and extracted with methylene chloride. The combined organic extracts are washed sequentially with water, saturated sodium hydrogen carbonate solution and water, dried over anhydrous sodium sulfate, and concentrated in vacuo to give the title product as a tan oil (1.95 g) which is identified by NMR spectral analyses.

Using essentially the same procedure, the following compound is obtained:

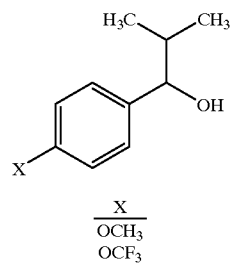

| X |
|---|
| OCH$_3$ |
| OCF$_3$ |

EXAMPLE 7

Preparation of 1-(p-Ethyoxyphenyl)-2-methylpropyl trifluoroacetate

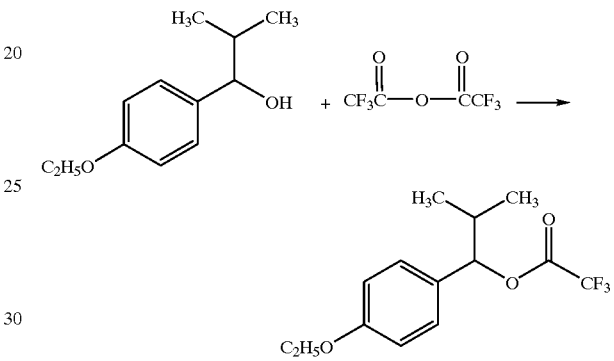

A mixture of trifluoroacetic anhydride (18 mL) in carbon tetrachloride is cooled with an ice-water bath, treated portionwise with a solution of p-ethoxy-α-isopropylbenzyl alcohol (9.0 g) in carbon tetrachloride, stirred at room temperature for 1 hour, concentrated in vacuo, diluted with carbon tetrachloride, and concentrated in vacuo to give the title product as a brown oil (13.23 g) which is identified by NMR spectral analysis.

Using essentially the same procedure, the following compound is obtained:

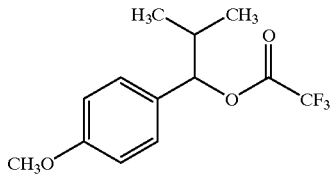

EXAMPLE 8

Preparation of p-[2,3-Difluoro-1-isopropyl-4-(m-phenoxyphenyl)-2-buten-1-yl]phenol, (E)-

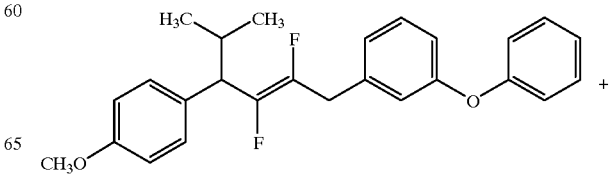

-continued

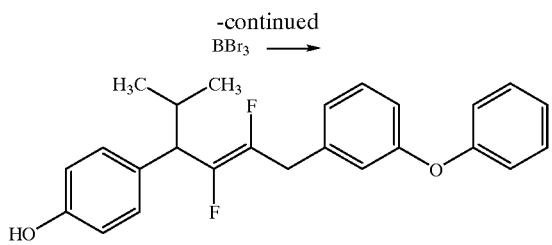

A solution of 2,3-difluoro-4-(p-methoxyphenyl)-5-methyl-1-(m-ph[]enoxyphenyl)-2-hexene, (E)-(0.408 g, 0.001 mol) in methylene chloride is cooled to −10° C., treated dropwise with a 1 M solution of boron tribromide in methylene chloride (1.0 mL, 0.001 mol), stirred overnight at room temperature, cooled, diluted with methanol, and concentrated in vacuo to obtain a residue. The residue is dissolved in methylene chloride. The resultant solution is washed sequentially with saturated sodium hydrogen carbonate solution and water, dried over anhydrous sodium sulfate, and concentrated in vacuo to obtain a brown oil. Column chromatography of the oil using silica gel and methylene chloride gives the title product as a pale, yellow oil (0.355 g) which is identified by NMR spectral analyses.

EXAMPLE 9

Preparation of 4-[p-(Difluoromethoxy)phenyl]-2,3-difluoro-5-methyl-1-(m-phenoxyphenyl)-2-hexene, (E)-

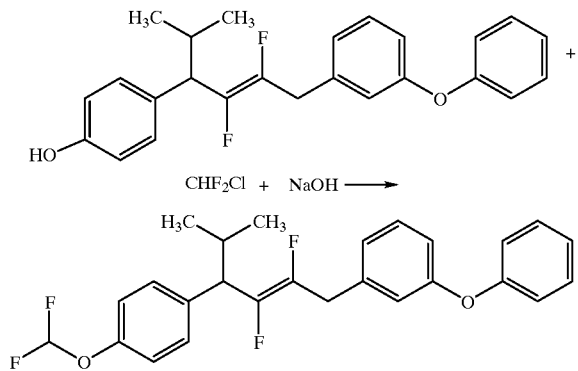

A mixture of p-[2,3-difluoro-1-isopropyl-4-(m-phenoxyphenyl)-2-buten-1-yl]phenol, (E)-(0.173 g), dioxane (6 mL) and water (4.5 mL) is treated sequentially with difluorochloromethane (70 drops) and sodium hydroxide (0.217 g), stirred at 70° C. for 1 hour, cooled, treated with additional difluorochloromethane (50 drops) and sodium hydroxide (0.245 g), heated at 58–66° C. for 3 hours, cooled, treated with additional difluorochloromethane (50 drops) and sodium hydroxide (0.185 g), heated for an additional 2.5 hours, stirred overnight at room temperature, and diluted with water. The resultant aqueous mixture is extracted with methylene chloride. The combined organic extracts are washed with water, dried over anhydrous sodium sulfate, and concentrated in vacuo to obtain a light brown oil. Column chromatography of the oil using silica gel and methylene chloride gives the title product as a colorless oil (0.134 g) which is identified by NMR spectral analyses.

EXAMPLE 10

Insecticidal and Acaricidal Evaluation of Test Comounds

Test solutions are prepared by dissolving the test compound in a 35% acetone in water mixture to give a concentration of 10,000 ppm. Subsequent dilutions are made with water as needed.

*Spodoptera eridania*, 3rd Instar Larvae, Southern Armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 3rd instar caterpillars. At 5 days, observations are made of mortality, reduced feeding, or any interference with normal molting.

*Diabrotica virgifera vircifera* Leconte, 3rd Instar Western Corn Rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten 3rd instar rootworms are added to each jar and the jars are loosely capped to allow air exchange for the larvae. The treatments are held for 5 days when mortality counts are made. Missing larvae are presumed dead, since they decompose rapidly and cannot be found. The concentrations of active ingredient used in this test correspond approximately to 50 kg/ha.

*Heliothis virenscens,* 3rd Instar Tobacco Budworm (TBW)

Cotton cotyledons are dipped in the test solution and allowed to dry in a hood. When dry, each is cut into quarters and ten sections are placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Aphis fabae*, Mixed Instar, Bean Aphid (BA)

Pots containing single nasturtium plants (Tropaeolum sp.) about 5 cm tall are infested with about 100–200 aphids one day before the test. Each pot is sprayed with the test solution for 2 revolutions of a 4 rpm turntable in a hood. The spray is directed to give complete coverage of the plants and aphids. The sprayed pots are set on their sides on white trays and held for 2 days, following which mortality estimates are made.

*Tetranychus urticae* (OP-Resistant Strain), 2-Spotted Spider Mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made.

The tests are rated according to the scale shown below and the data obtained are shown in Table I.

Compounds employed in the above-described evaluations are given a compound number and identified by name. Data in Table I are reported by compound number.

| Rating Scale |
|---|
| 0 = no effect |
| 1 = 10–25% kill |
| 2 = 26–35% kill |
| 3 = 36–45% kill |
| 4 = 46–55% kill |
| 5 = 56–65% kill |
| 6 = 66–75% kill |
| 7 = 76–85% kill |
| 8 = 86–99% kill |
| 9 = 100% kill |

| COMPOUNDS EVALUATED AS INSECTICIDAL AND ACARICIDAL AGENTS | |
|---|---|
| Compound Number | |
| 1 | 4-(p-Chlorophenyl)-2,3-difluoro-5-methyl-1-(m-phenoxyphenyl)-2-hexene, (E)- |
| 2 | 4-(p-Chlorophenyl)-2,3-difluoro-1-(4-fluoro-3-phenoxyphenyl)-5-methyl-2-hexene, (E)- |
| 3 | 2,3-Difluoro-5-methyl-1-(m-phenoxyphenyl)-4-[p-(trifluoromethoxy)phenyl]-2-hexene, (E)- |
| 4 | 4-(p-Ethoxyphenyl)-2,3-difluoro-1-(m-phenoxyphenyl)-5-methyl-2-hexene, (E)- |
| 5 | 4-(p-Ethoxyphenyl)-2,3-difluoro-1-(4-fluoro-3-phenoxyphenyl)-5-methyl-2-hexene, (E)- |
| 6 | 2,3-Difluoro-1-(4-fluoro-3-phenoxyphenyl)-5-methyl-4-[p-(trifluoromethoxy)phenyl]-2-hexene, (E)- |
| 7 | 2,3-Difluoro-4-(p-fluorophenyl)-5-methyl-1-(m-phenoxyphenyl)-2-hexene, (E)- |
| 8 | 2,3-Difluoro-1-(4-fluoro-3-phenoxyphenyl)-4-(p-fluorophenyl)-5-methyl-2-hexene, (E)- |

TABLE I

| | Insecticidal And Acaricidal Evaluations | | | | |
|---|---|---|---|---|---|
| Compound Number | SAW (100 ppm) | WCR (50 ppm) | TBW (100 ppm) | BA (100 ppm) | TSM (100 ppm) |
| 1 | 9 | 9 | 9 | 4 | 0 |
| 2 | 9 | 9 | 9 | 7 | 0 |
| 3 | 9 | 9 | 9 | 2 | 5 |
| 4 | 9 | 9 | 9 | 8 | 0 |
| 5 | 9 | 9 | 9 | 7 | 0 |
| 6 | 9 | 9 | 9 | 8 | 9 |
| 7 | 9 | 9 | 9 | 9 | 0 |
| 8 | 9 | 9 | 9 | 8 | 7 |

We claim:

1. A compound having the structural formula

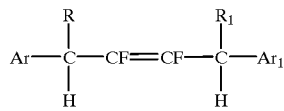

wherein

Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is hydrogen, $C_1$–$C_4$alkyl, $C_1$–$C_4$haloalkyl, $C_3$–$C_6$cycloalkyl or $C_3$–$C_6$halocycloalkyl;

$R_1$ is hydrogen, F, Cl, Br, cyano or $OR_2$;

$R_2$ is hydrogen or $C_1$–$C_4$alkyl; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and
the optical isomers thereof, and
the (E)- and (Z)-isomers thereof.

2. The compound according to claim 1 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is $C_1$–$C_4$alkyl, $C_1$–$C_4$haloalkyl, $C_3$–$C_6$cycloalkyl or $C_3$–$C_6$halocycloalkyl; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

3. The compound according to claim 2 wherein
R is isopropyl, trifluoromethyl or cyclopropyl;
$R_1$ is hydrogen; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

4. The compound according to claim 3 wherein
R is isopropyl.

5. The compound according to claim 4 selected from the group consisting of
4-(p-chlorophenyl)-2,3-difluoro-5-methyl-1-(m-phenoxyphenyl)-2-hexene, (E)-;
4-(p-chlorophenyl)-2,3-difluoro-1-(4-fluoro-3-phenoxyphenyl)-5-methyl-2-hexene, (E)-;
2,3-difluoro-5-methyl-1-(m-phenoxyphenyl)-4-[p-(trifluoromethoxy)phenyl]-2-hexene, (E)-;
4-(p-ethoxyphenyl)-2,3-difluoro-1-(m-phenoxyphenyl)-5-methyl-2-hexene, (E)-;
4-(p-ethoxyphenyl)-2,3-difluoro-1-(4-fluoro-3-phenoxyphenyl)-5-methyl-2-hexene, (E)-;
2,3-difluoro-1-(4-fluoro-3-phenoxyphenyl)-S-methyl-4-[p-(trifluoromethoxy)phenyl]-2-hexene, (E)-;
2,3-difluoro-4-(p-fluorophenyl)-5-methyl-1-(m-phenoxyphenyl)-2-hexene, (E)-; and
2,3-difluoro-1-(4-fluoro-3-phenoxyphenyl)-4-(p-fluorophenyl)-5-methyl-2-hexene, (E)-.

6. A method for the control of insect or acarid pests which comprises contacting said pests or their food supply, habitat or breeding grounds with a pesticidally effective amount of a compound having the structural formula

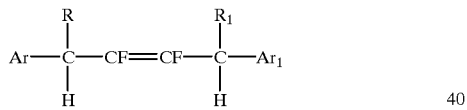

wherein
Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is hydrogen, $C_1$–$C_4$alkyl, $C_1$–$C_4$haloalkyl, $C_3$–$C_6$cycloalkyl or $C_3$–$C_6$halocycloalkyl;
$R_1$ is hydrogen, F, Cl, Br, cyano or $OR_2$;
$R_2$ is hydrogen or $C_1$–$C_4$alkyl; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and
the optical isomers thereof, and
the (E)- and (Z)-isomers thereof.

7. The method according to claim 6 wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is $C_1$–$C_4$alkyl, $C_1$–$C_4$haloalkyl, $C_3$–$C_6$cycloalkyl or $C_3$–$C_6$halocycloalkyl; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

8. The method according to claim 7 wherein
R is isopropyl, trifluoromethyl or cyclopropyl;
$R_1$ is hydrogen; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

9. The method according to claim 8 wherein
R is isopropyl.

10. The method according to claim 9 wherein the compound is selected from the group consisting of
4-(p-chlorophenyl)-2,3-difluoro-5-methyl-1-(m-phenoxyphenyl)-2-hexene, (E)-;
4-(p-chlorophenyl)-2,3-difluoro-1-(4-fluoro-3-phenoxyphenyl)-5-methyl-2-hexene, (E)-;
2,3-difluoro-5-methyl-1-(m-phenoxyphenyl)-4-[p-(trifluoromethoxy)phenyl]-2-hexene, (E)-;

4-(p-ethoxyphenyl)-2,3-difluoro-1-(m-phenoxyphenyl)-5-methyl-2-hexene, (E)-;

4-(p-ethoxyphenyl)-2,3-difluoro-1-(4-fluoro-3-phenoxyphenyl)-5-methyl-2-hexene, (E)-;

2,3-difluoro-1-(4-fluoro-3-phenoxyphenyl)-5-methyl-4-[p-(trifluoromethoxy)phenyl]-2-hexene, (E)-;

2,3-difluoro-4-(p-fluorophenyl)-5-methyl-1-(m-phenoxyphenyl)-2-hexene, (E)-; and 2,3-difluoro-1-(4-fluoro-3-phenoxyphenyl)-4-(p-fluorophenyl)-5-methyl-2-hexene, (E)-.

11. A method for the protection of growing plants from attack or infestation by insect or acarid pests which comprises applying to the foliage of the plants, or to the soil or water in which they are growing, a pesticidally effective amount of a compound having the structural formula

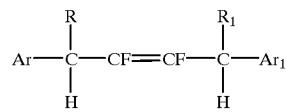

wherein

Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is hydrogen, $C_1$–$C_4$alkyl, $C_1$–$C_4$haloalkyl, $C_3$–$C_6$cycloalkyl or $C_3$–$C_6$halocycloalkyl;

$R_1$ is hydrogen, F, Cl, Br, cyano or $OR_2$;

$R_2$ is hydrogen or $C_1$–$C_4$alkyl; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$ alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and the optical isomers thereof, and the (E)- and (Z)-isomers thereof.

12. The method according to claim 11 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is $C_1$–$C_4$alkyl, $C_1$–$C_4$haloalkyl, $C_3$–$C_6$cycloalkyl or $C_3$–$C_6$halocycloalkyl; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

13. The method according to claim 12 wherein

R is isopropyl, trifluoromethyl or cyclopropyl;

$R_1$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

14. The method according to claim 13 wherein

R is isopropyl.

15. The method according to claim 14 wherein the compound is selected from the group consisting of 4-(p-chlorophenyl)-2,3-difluoro-5-methyl-1-(m-phenoxyphenyl)-2-hexene, (E)-;

4-(p-chlorophenyl)-2,3-difluoro-1-(4-fluoro-3-phenoxyphenyl)-5-methyl-2-hexene, (E)-;

2,3-difluoro-5-methyl-1-(m-phenoxyphenyl)-4-[p-(trifluoromethoxy)phenyl]-2-hexene, (E)-;

4-(p-ethoxyphenyl)-2,3-difluoro-1-(m-phenoxyphenyl)-5-methyl-2-hexene, (E)-;

4-(p-ethoxyphenyl)-2,3-difluoro-1-(4-fluoro-3-phenoxyphenyl)-5-methyl-2-hexene, (E)-;

2,3-difluoro-1-(4-fluoro-3-phenoxyphenyl)-5-methyl-4-[p-(trifluoromethoxy)phenyl]-2-hexene, (E)-;

2,3-difluoro-4-(p-fluorophenyl)-5-methyl-1-(m-phenoxyphenyl)-2-hexene, (E)-; and 2,3-difluoro-1-(4-fluoro-3-phenoxyphenyl)-4-(p-fluorophenyl)-5-methyl-2-hexene, (E)-.

16. The method according to claim 11 wherein the compound is applied to the plants, or to the soil or water in which they are growing, at a rate of about 0.1 kg/ha to 4.0 kg/ha.

17. A composition for the control of insect or acarid pests which comprises an agronomically acceptable carrier and a pesticidally effective amount of a compound having the structural formula

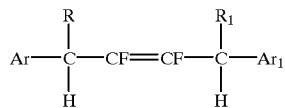

wherein
- Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups,
  - 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  - a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
- R is hydrogen, $C_1$–$C_4$alkyl, $C_1$–$C_4$haloalkyl, $C_3$–$C_6$cycloalkyl or $C_3$–$C_6$halocycloalkyl;
- $R_1$ is hydrogen, F, Cl, Br, cyano or $OR_2$;
- $R_2$ is hydrogen or $C_1$–$C_4$alkyl; and
- $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  - phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  - biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  - phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  - benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  - benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  - benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  - 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  - a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and the optical isomers thereof, and
the (E)- and (Z)-isomers thereof.

18. The composition according to claim 17 wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is $C_1$–$C_4$alkyl, $C_1$–$C_4$haloalkyl, $C_3$–$C_6$cycloalkyl or $C_3$–$C_6$halocycloalkyl; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
- 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
- 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

19. The composition according to claim 18 wherein
R is isopropyl, trifluoromethyl or cyclopropyl;

$R_1$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

20. The composition according to claim 19 wherein
R is isopropyl.

21. A compound having the structural formula

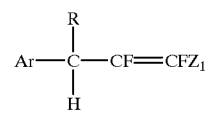

wherein
- Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
  - 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  - a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
- R is hydrogen, $C_1$–$C_4$alkyl, $C_1$–$C_4$haloalkyl, $C_3$–$C_6$cycloalkyl or $C_3$–$C_6$halocycloalkyl;
- $Z_1$ is hydrogen or F, and the optical isomers thereof, and the (E)- and (Z)-isomers thereof;

with the proviso that when Ar is phenyl and R is $CF_3$, $Z_1$ is not F.

22. The compound according to claim 21 wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and R is $C_1$–$C_4$alkyl, $C_1$–$C_4$haloalkyl, $C_3$–$C_6$cycloalkyl or $C_3$–$C_6$halocycloalkyl.

23. A compound having the structural formula:

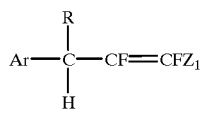

wherein
Ar is phenyl optionally substituted with any combination of from one to three halogen, $C_1$–$C_4$ alkyl, $C_1$–$C_4$ haloalkyl, $C_1$–$C_4$ alkoxy or $C_1$–$C_4$ haloalkoxy groups;
R is isopropyl;
$Z_1$ is hydrogen or F, and
the optical isomers thereof, and
the (E)- and (Z)-isomers thereof.

24. A process for the preparation of a compound having the structural formula

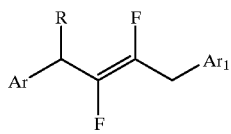

wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is hydrogen, $C_1$–$C_4$alkyl, $C_1$–$C_4$haloalkyl, $C_3$–$C_6$cycloalkyl or $C_3$–$C_6$halocycloalkyl; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises reacting a 3-aryl-1,1,2-trifluoro-1-propene compound having the structural formula

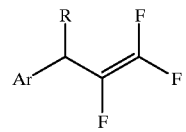

wherein Ar and R are as described above with sodium bis(2-methoxyethoxy)aluminum hydride and a mineral acid to form a 3-aryl-1,2-difluoro-1-propene compound having the structural formula

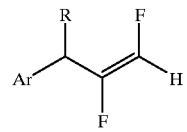

wherein Ar and R are as described above, and sequentially reacting the 3-aryl-1,2-difluoro-1-propene compound with an alkyllithium compound, zinc chloride, tetrakis (triphenylphosphine)palladium(0) and a substituted methyl halide compound having the structural formula

wherein Z is Cl, Br or I and $Ar_1$ is as described above.

25. The process according to claim 24 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is $C_1$–$C_4$alkyl, $C_1$–$C_4$haloalkyl, $C_3$–$C_6$cycloalkyl or $C_3$–$C_6$halocycloalkyl; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

26. The process according to claim 25 wherein

R is isopropyl; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

* * * * *